(12) United States Patent
Hembrough et al.

(10) Patent No.: US 10,617,717 B2
(45) Date of Patent: Apr. 14, 2020

(54) METHODS OF TREATING LUNG CANCER BY PREDICTING RESPONDERS TO CISPLATIN-PEMETREXED COMBINATION THERAPY

(71) Applicant: Expression Pathology, Inc., Rockville, MD (US)

(72) Inventors: Todd Hembrough, Gaithersburg, MD (US); Fabiola Cecchi, Washington, DC (US); Jean-Charles Soria, Villejuif (FR)

(73) Assignee: Expression Pathology, Inc., Rockville, MD (US)

( * ) Notice: Subject to any disclaimer, the term of this patent is extended or adjusted under 35 U.S.C. 154(b) by 0 days.

(21) Appl. No.: 15/831,343

(22) Filed: Dec. 4, 2017

(65) Prior Publication Data

US 2018/0177825 A1    Jun. 28, 2018

Related U.S. Application Data

(60) Provisional application No. 62/429,859, filed on Dec. 4, 2016.

(51) Int. Cl.
| | | |
|---|---|---|
| *A61K 33/24* | (2019.01) | |
| *A61P 35/00* | (2006.01) | |
| *G01N 33/574* | (2006.01) | |
| *A61K 31/519* | (2006.01) | |
| *G01N 33/68* | (2006.01) | |

(52) U.S. Cl.
CPC ............ *A61K 33/24* (2013.01); *A61K 31/519* (2013.01); *A61P 35/00* (2018.01); *G01N 33/57423* (2013.01); *G01N 33/6848* (2013.01); *G01N 2333/47* (2013.01); *G01N 2333/4704* (2013.01); *G01N 2333/705* (2013.01); *G01N 2333/91017* (2013.01); *G01N 2800/52* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 7,473,532 | B2 | 1/2009 | Darfler et al. |
| 7,501,286 | B2 | 3/2009 | Gygi et al. |
| 7,632,686 | B2 | 12/2009 | Anderson |
| 9,372,195 | B2 | 6/2016 | Krizman et al. |
| 2010/0029005 | A1 | 2/2010 | Kamiie et al. |
| 2012/0171305 | A1 | 7/2012 | Kandioler |
| 2014/0011728 | A1 | 1/2014 | Drum et al. |
| 2014/0120543 | A1 | 5/2014 | Olaussen et al. |
| 2014/0162888 | A1 | 6/2014 | Kuslich et al. |
| 2015/0376678 | A1 | 12/2015 | Krizman et al. |
| 2016/0263187 | A1 | 9/2016 | Lander et al. |
| 2016/0341713 | A1 | 11/2016 | Krizman et al. |
| 2018/0177825 | A1 | 6/2018 | Hembrough et al. |

FOREIGN PATENT DOCUMENTS

| | | | |
|---|---|---|---|
| JP | 2006-519996 A | 8/2006 | |
| JP | 2014-507640 A | 3/2014 | |
| WO | 2007/055116 A1 | 5/2007 | |
| WO | 2011087865 A1 | 7/2011 | |
| WO | 2012142411 A1 | 10/2012 | |
| WO | 2013040142 A2 | 3/2013 | |
| WO | WO 2015/168483 | * 11/2015 | ............... C12Q 1/68 |
| WO | 2016004233 A2 | 1/2016 | |

OTHER PUBLICATIONS

Zarogoulidis et al (J Thorac Dis 5(S4):S389-S396, 2013) (Year: 2013).*
Novello et al (J Clin Oncol 29:e17514, 2011) (Year: 2011).*
Adjei (Clip Lung Cancer 5(Suppl 2):S51-S55, 2004) (Year: 2004).*
Nunez et al (J Thorac Oncol 7:833-840, 2012) (Year: 2012).*
GenBank AAL56574 (available as of 2001) (Year: 2001).*
NCBI Reference Sequence NP_001341796 (available as of 1995) (Year: 1995).*
GenBank ABC50001 (available as of 2005) (Year: 2005).*
GenBank AAB31700 (available as of 1994) (Year: 1994).*
International Search Report and Written Opinion in corresponding International Application No. PCT/US17/64562.
U.S. Appl. No. 15/323,689, filed Jan. 3, 2017.
U.S. Appl. No. 15/343,976, filed Nov. 4, 2016.
Spratlin, J., et al., The Absence of Human Equilibrative Nucleoside Transporter 1 is Associated with Reduced Survival in Patients With Gemcitabine-Treated Pancreas Adenocarcinoma (2004), Clinical Cancer Research, 10:6956-6961.
Notice of Preliminary Rejection from Korean Patent Application No. 10-2017-700572 (English translation), 7 pages.
Communication pursuant to Article 94(3) EPC for European Patent Application No. 15814792.6 dated Mar. 8, 2019.
Steiner, C., et al., "Applications of mass spectrometry for quantitative protein analysis in formalin-fixed paraffin-embedded tissues" (2014), Proteomics Journal, 14:441-451.
Expression Pathology, Liquid Tissue MS Protein Prep Kit for the isolation of proteins and peptides from formalin fixed tissue in preparation for mass spectrometry analysis (2009), www.expressionpathology.com/pdf/LiquidTissueManualV146.pdf>); pp. 5-6.

(Continued)

*Primary Examiner* — Craig D Ricci
(74) *Attorney, Agent, or Firm* — Harness Dickey & Pierce P.L.C.

(57) ABSTRACT

Methods are provided for identifying whether a lung tumor will be responsive to treatment with the combination of the therapeutic agents cisplatin and pemetrexed. Specified ERCC1, TS, p16, and FRα fragment peptides are precisely detected and quantitated by SRM-mass spectrometry directly in lung tumor cells collected from lung tumor tissue that was obtained from a cancer patient and compared to reference levels in order to determine if the lung cancer patient will positively respond to treatment with the combination of cisplatin and pemetrexed therapeutic agents.

10 Claims, 4 Drawing Sheets
Specification includes a Sequence Listing.

(56) References Cited

OTHER PUBLICATIONS

International Search Report and Written Opinion in Application No. PCT/US2015/038874, dated Dec. 21, 2015, 16 pages.
Murata, Y., el al.: "Human equilibrative nucleoside transporter 1 expression is a strong independent prognostic factor in UICC T3-T4 pancreatic cancer patients treated with preoperative gemcitabine-based chemoradiotherapy," Journal of Hepatobiliary Pancreatic Science, (2012), 19(4):4.
NCBI Reference Sequence: NP 001071643.1; equilibrative nucleoside transporter 1 (*Homo sapiens*). Apr. 20, 2014 (Retrieved from the Internet Sep. 24, 2015: <http://www.ncbi.nlm.nih.gov/protein/118582262?satkey= 18620465>]; p. 1, 2.
Reyes, G., et al.: "The Equilibrative Nucleoside Transporter (ENT1) can be phosphorylated at multiple sites by PKC and PKA ", Mol Membr Biol., (2011), 28(6):412-26, Abstract, p. 415, col. 2; p. 416, col. 2; p. 422, Fig 6 and its legend.
Supplementary European Search Report in corresponding European Application No. 15814792.6, dated Nov. 3, 2017 (18 pages).
Whiteaker, J., et al., Journal of Proteome Research (2007), 6:3962-3975.
Domanski, D., et al., Analytical Chemistry (2010), 82:5610-5620.
Atsriku, C., et al., Molecular & Cellular Proteomics (2008), 8:467-480.
Reyes, G., et al., Protein Expression and Purification (2010), 73:1-9.
Oguri, T., et al., Cancer Letters (2007), 256:112-119.
Office Action for Chinese Application No. 201580045634.1 dated Nov. 5, 2018 (with English translation), 13 pages.
Japanese Office Action dated Mar. 15, 2019 issued in Japanese Patent Application No. 2017-500071 (with English translation), 10 pages.
Winefield, R., et al., Anal Biochem. (2009), 395(2):217-223.
Levallet G., et al., Mol Cancer Ther. (2012), 11(5):1203-13.
Extended European Search Report dated Feb. 8, 2018 issued in corresponding application EP 3164708, 16 pages.
International Preliminary Report of Patentability dated Jan. 3, 2017 issued in corresponding application PCT/US2015/038874, 10 pages.
Korean Office Action dated May 30, 2019 issued in Korean Patent Application No. 10-2017-7002572 (with English translation), 10 pages.
Wright, M., et al., Molecular and Cellular Proteomics (2005), 4(4):545-554.
Ceppi, P., et al., Annals of Oncology (2006), 17:1818-1825.
Su, C., et al., Med Oncol (2011), 28:1411-1417.
Database Registry, RN 1338578-34-9.
Pesta, M., et al., Anticancer Research (2012), 32:5003-5010.
Chinese Office Action dated Jun. 21, 2019 issued in Chinese Patent Application No. 201580045634.1 (with English translation), 17 pages.
Office Action dated Oct. 9, 2018 issued in U.S. Appl. No. 15/343,976, 11 pages.
Office Action dated Apr. 8, 2019 issued in U.S. Appl. No. 15/323,689, 11 pages.
Prieto, "Liquid Tissue: proteomic profiling of formalin-fixed tissues," BioTechniques 38:S32-S35 (Jun. 2005)
Office Action dated Sep. 9, 2019 issued in co-pending U.S. Appl. No. 15/323,689 (14 pages).
U.S. Appl. No. 16/251,409, filed Jan. 18, 2019.

* cited by examiner

SEQUENCE LISTING

<160> NUMBER OF SEQ ID NOS: 4

<210> SEQ ID NO 1
<211> LENGTH: 12
<212> TYPE: PRT
<213> ORGANISM: Homo sapiens

<400> SEQUENCE: 1

Glu Gly Val Pro Gln Pro Ser Gly Pro Pro Ala Arg
1               5                   10

<210> SEQ ID NO 2
<211> LENGTH: 14
<212> TYPE: PRT
<213> ORGANISM: Homo sapiens

<400> SEQUENCE: 2

Glu Glu Gly Asp Leu Gly Pro Val Tyr Gly Phe Gln Trp Arg
1               5                   10

<210> SEQ ID NO 3
<211> LENGTH: 17
<212> TYPE: PRT
<213> ORGANISM: Homo sapiens

<400> SEQUENCE: 3

Ala Leu Leu Glu Ala Gly Ala Leu Pro Asn Ala Pro Asn Ser Tyr Gly Arg
1               5                   10                  15

<210> SEQ ID NO 4
<211> LENGTH: 7
<212> TYPE: PRT
<213> ORGANISM: Homo sapiens

<400> SEQUENCE: 4

Asp Val Ser Tyr Leu Tyr Arg
1               5

METHODS OF TREATING LUNG CANCER BY PREDICTING RESPONDERS TO CISPLATIN-PEMETREXED COMBINATION THERAPY

CROSS-REFERENCE TO RELATED APPLICATIONS

This application claims priority to provisional application Ser. No. 62/429,859, filed Dec. 4, 2016, the contents of which are hereby incorporated by reference in their entirety. This application also contains a sequence listing submitted electronically via EFS-web, which serves as both the paper copy and the computer readable form (CRF) and consists of a file entitled "3900_0065C_Sequence_listing.txt", which was created on Mar. 5, 2018, which is 4,096 bytes in size, and which is also incorporated by reference in its entirety.

INTRODUCTION

Improved methods for treating cancer patients are provided by assaying tumor tissue from patients and identifying those patients most likely to respond to treatment with cisplatin, which is a member of the platinum-based class of chemotherapeutic, in combination with pemetrexed, which is a member of the antifolate class of drugs. More specifically, methods are provided for identifying those lung cancer patients most likely to respond to treatment with the combination of cisplatin+pemetrexed chemotherapy agents by determining specific levels of a set of specific proteins directly in tumor cells derived from patient tumor tissue using SRM mass spectrometry. The proteins that are measured are ERCC1, TS, p16, and FRα.

Cisplatin, also known as cisplatinum, platamin, and neoplatin, is a member of a class of platinum-containing anticancer drugs, which also includes carboplatin and oxaliplatin. Once inside the cancer cell these platinum therapeutic agents bind to and cause crosslinking of DNA which damages DNA ultimately triggering apoptosis (programmed cell death) and death to cancer cells. Nucleotide excision repair (NER) is the primary DNA repair mechanism that removes the therapeutic platinum-DNA adducts from the tumor cell DNA.

Pemetrexed, also known as Alimta, is chemically similar to folic acid and is in the class of chemotherapy drugs called folate antimetabolites. It works by inhibiting three enzymes used in purine and pyrimidine synthesis-thymidylate synthase (TS), dihydrofolate reductase (DHFR), and glycinamide ribonucleotide formyltransferase (GARFT). By inhibiting the formation of precursor purine and pyrimidine nucleotides, pemetrexed prevents the formation of DNA and RNA, which are required for the growth and survival of both normal cells and cancer cells.

ERCC-1 is a protein that is a critical component of the NER pathway. ERCC1 forms the ERCC1-XPF enzyme complex that participates in DNA repair and DNA recombination and is capable of removing DNA damage caused by cisplatin and other members of the platinum-based chemotherapeutic agents. Patients with non-small cell lung carcinoma (NSCLC) that receive no further therapy have a better chance of survival if the tumor cells within their tumor tissue are ERCC1-positive rather than if they are ERCC1-negative. Accordingly, ERCC1 positivity is a favorable prognostic marker, referring to how the disease will proceed if not treated further. ERCC1-positive NSCLC tumors do not benefit from platinum-based chemotherapy. However, ERCC1-negative NSCLC tumors, which are prognostically worse without treatment, derive substantial benefit from cisplatin-based chemotherapy. Accordingly, high ERCC1 is a negative predictive marker, referring to how a cancer will respond to a specific type of treatment.

TS, also known as thymidylate synthetase and TYMS, is an enzyme that catalyzes the conversion of deoxyuridine monophosphate (dUMP) to deoxythymidine monophosphate (dTMP). Thymidine is one of the nucleotides in DNA. With inhibition of TS, an imbalance of deoxynucleotides and increased levels of dUMP arise, both of which cause DNA damage and ultimately cell death. TS-negative NSCLC tumors, prognostically worse without treatment, derive substantial benefit from pemetrexed-based chemotherapy. High TS is thus a negative predictive marker, referring to how a cancer will respond to a specific type of treatment.

P16, also known as cyclin-dependent kinase inhibitor 2A and multiple tumor suppressor 1, is a tumor suppressor protein that plays an important role in cell cycle regulation. P16 functions by decelerating cell progression from G1 phase to S phase, and therefore acts as a tumor suppressor that is implicated in the prevention of cancers, notably melanoma, oropharyngeal squamous cell carcinoma, cervical cancer, and esophageal cancer. The p16 gene is frequently mutated or deleted in a wide variety of tumors. Expression of p16 and its involvement through the ROS pathway, chemotherapy-induced DNA damage, and/or cellular senescence leads to the buildup of p16 in cells and is implicated in aging of cells. The mechanism by which the combination of cisplatin and pemetrexed relates to expression and/or function of the p16 protein in cancer cells is unknown.

FRα, also known as folate receptor alpha and FOLR1, is a receptor protein that is abnormally present on many types of tumor cells, including lung cancer cells. The function of the FRα protein is to move folate and reduced folic acid derivatives into a cell which helps control how a healthy normal cell grows, divides, and repairs itself. However, in some cancers, including lung cancer, the cancer cells abnormally express the FRα protein and the cancer cells grow and divide in an uncontrolled way. Because the pemetrexed agent enters the cancer cell via the FRα protein it therefore is useful for a clinician to know the expression level of the FRα protein in a patient's cancer cells. The higher the expression of FRα the more pemetrexed can enter the tumor cell and thus cause harm and kill the tumor cell.

ERCC1, TS, p16 and FRα are therefore prognostic predictors of outcome and their expression levels are predictive of therapeutic efficacy in patients with non-small cell lung cancer; as such, measuring expression levels of these proteins can provide information about chemotherapy treatment strategies of cancer, leading to improved treatment outcomes. The presence and/or quantitative levels of ERCC1, TS, p16 and FRα protein expression in the tumor tissue is determined by quantitating a specified peptide derived from subsequences of each of the ERCC1, TS, p16 and FRα full-length proteins. The measurement is carried out directly in patient-derived tumor cells using the methodology of SRM mass spectrometry. If expression of the ERCC1 protein is detected by SRM mass spectrometry a lung cancer patient is less likely to respond in a positive manner to the combination of cisplatin/pemetrexed. If TS protein expression is detected a lung cancer patient is less likely to respond to the cisplatin/pemetrexed combination. If p16 protein expression is quantitated below a specified reference level a lung cancer patient is more likely to respond favorably to the cisplatin/pemetrexed combination. If FRα protein expression is quantitated above a specified level a lung cancer patient is more likely to respond favorably to the cisplatin/pemetrexed combination. In this way, measurement of one or more of the listed proteins can be used as part of an improved treatment regimen by guiding treatment selection. Measurement of two, three, or all four of the proteins can lead to a more robust prediction than measurement of a single protein. Thus, for example, the following combinations of proteins can be measured:

ERCC1 and TS
ERCC1 and p16
ERCC1 and FRα
TS and p16
TS and FRα
p16 and FRα
ERCC1, TS, and p16
ERCC1, TS, and FRα
TS, p16 and FRα
ERCC1, TS, p16 and FRα

SUMMARY OF THE INVENTION

Methods are provided for treating a patient suffering from lung cancer by quantifying the level of at least one of a group of peptides selected from the group consisting of: a specified ERCC1 fragment peptide, a specified TS fragment peptide, a specified p16 fragment peptide, and a specified FRα fragment peptide, in a protein digest prepared from a tumor sample obtained from the patient and calculating the level of the ERCC1, TS, p16, and/or FRα peptides in the sample. The peptide(s) may be quantified by selected reaction monitoring using mass spectrometry by comparing the level of the ERCC1, TS, p16, and/or FRα fragment peptides to a reference level that is defined for each peptide. The measured levels of the peptide are then compared to corresponding reference levels, and the patient is treated with a therapeutic regimen comprising an effective amount of the combination of cisplatin and pemetrexed therapeutic agents when: the level of the ERCC1 fragment peptide is below the reference level, or when the level of the TS fragment peptide is below the reference level, or when the level of the p16 fragment peptide is below the reference level, or when the level of the FRα fragment peptide is above the reference level. In certain embodiments, at least two, at least three, or all four of the fragment peptides are measured. The protein digest may include a protease digest such as a trypsin digest. The specified ERCC1 peptide may have the amino acid sequence as set forth as SEQ ID NO:1. The specified TS peptide may have the amino acid sequence as set forth as SEQ ID NO:2. The specified p16 peptide may have the amino acid sequence as set forth as SEQ ID NO:3. The specified FRα peptide may have the amino acid sequence as set forth as SEQ ID NO:4.

The tumor sample may be a cell, collection of cells, or a solid tissue, such as formalin fixed solid tissue, and/or paraffin embedded tissue.

The mode of mass spectrometry may be, for example, tandem mass spectrometry, ion trap mass spectrometry, triple quadrupole mass spectrometry, MALDI-TOF mass spectrometry, MALDI mass spectrometry, hybrid ion trap/quadrupole mass spectrometry and/or time of flight mass spectrometry and may be carried out using Selected Reaction Monitoring (SRM), Multiple Reaction Monitoring (MRM), Parallel Reaction Monitoring (PRM), intelligent Selected Reaction Monitoring (iSRM), and/or multiple Selected Reaction Monitoring (mSRM).

In these methods quantifying the specified ERCC1 fragment peptide may be achieved by, for example, by comparing to a spiked internal standard peptide of known amount, where both the native peptide in the biological sample and the internal standard peptide corresponds to the same amino acid sequence of the ERCC1 fragment peptide as shown in SEQ ID NO:1. The specified TS fragment peptide may be quantified by comparing to a spiked internal standard peptide of known amount, where both the native peptide in the biological sample and the internal standard peptide corresponds to the same amino acid sequence of the TS fragment peptide as shown in SEQ ID NO:2. The specified p16 fragment peptide may be quantified by comparing to a spiked internal standard peptide of known amount, where both the native peptide in the biological sample and the internal standard peptide corresponds to the same amino acid sequence of the p16 fragment peptide as shown in SEQ ID NO:3. The specified FRα fragment peptide may be quantified by comparing to a spiked internal standard peptide of known amount, where both the native peptide in the biological sample and the internal standard peptide corresponds to the same amino acid sequence of the FRα fragment peptide as shown in SEQ ID NO:4. In each case the internal standard peptide may be an isotopically labeled peptide, such as a peptide labeled with one or more heavy stable isotopes selected from $^{18}O$, $^{17}O$, $^{15}N$, $^{13}C$, $^{2}H$ or combinations thereof.

In the methods described herein the specified level of the ERCC1 peptide fragment may be 36±25 amol/ug protein analyzed, the specified level of the TS peptide fragment may be 150±50 or 150±25 amol/ug protein analyzed, the specified level of the p16 peptide fragment may be 117±50 or 117±25 amol/ug protein analyzed and/or the specified level of the FRα peptide fragment may be 1639±250, 1639±150, 1639±100, 1639±50 or 1639±25 amol/ug protein analyzed.

Detecting and quantitating the specified ERCC1, TS, p16, and/or FRα fragment peptides can be combined with detecting and quantitating other peptides from other proteins in multiplex so that the treatment decision about which agent used for treatment is based upon specific levels of the specified fragment peptide(s) in combination with other peptides/proteins in the biological sample.

DETAILED DESCRIPTION

Figure 1:
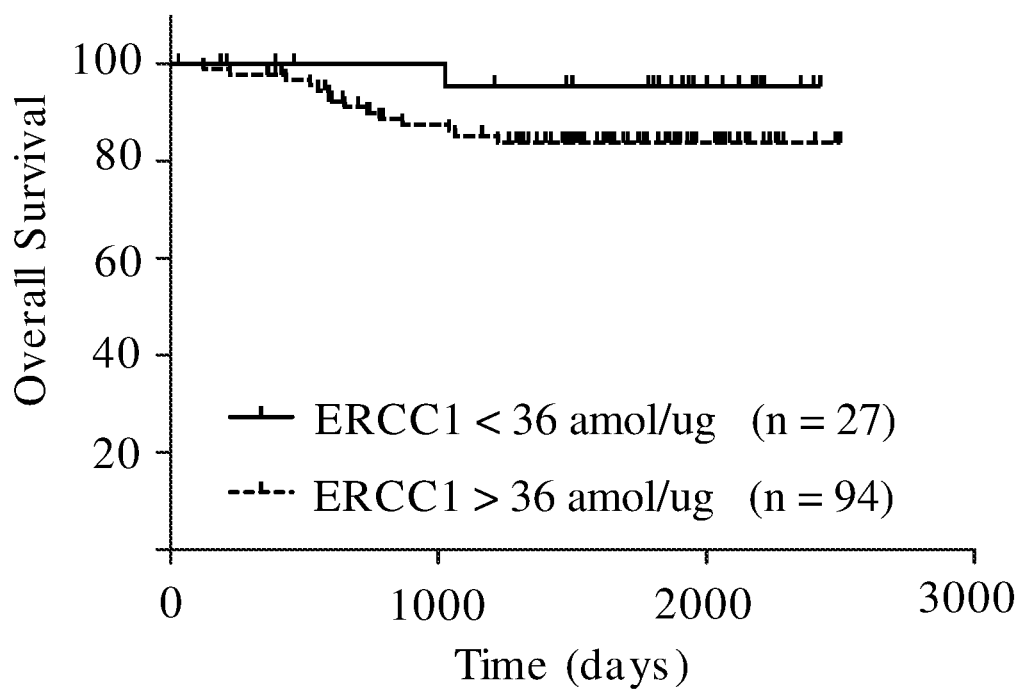
FIG. 1 shows the overall survival curve for NSCLC patients treated with the chemotherapy combination of cisplatin/pemetrexed in relation to ERCC1 protein expression levels. Those patients whose tumor cells express levels <36 amol/ug of ERCC1 fragment peptide have a more favorable outcome. This overall survival curve shows that those patients whose tumor cells express levels of the ERCC1 protein below 36 amol/ug protein analyzed have a much greater possibility of longer overall survival than those patients whose tumor cells express above 36 amol/ug when treated with the combination of cisplatin and pemetrexed.
Figure 2:
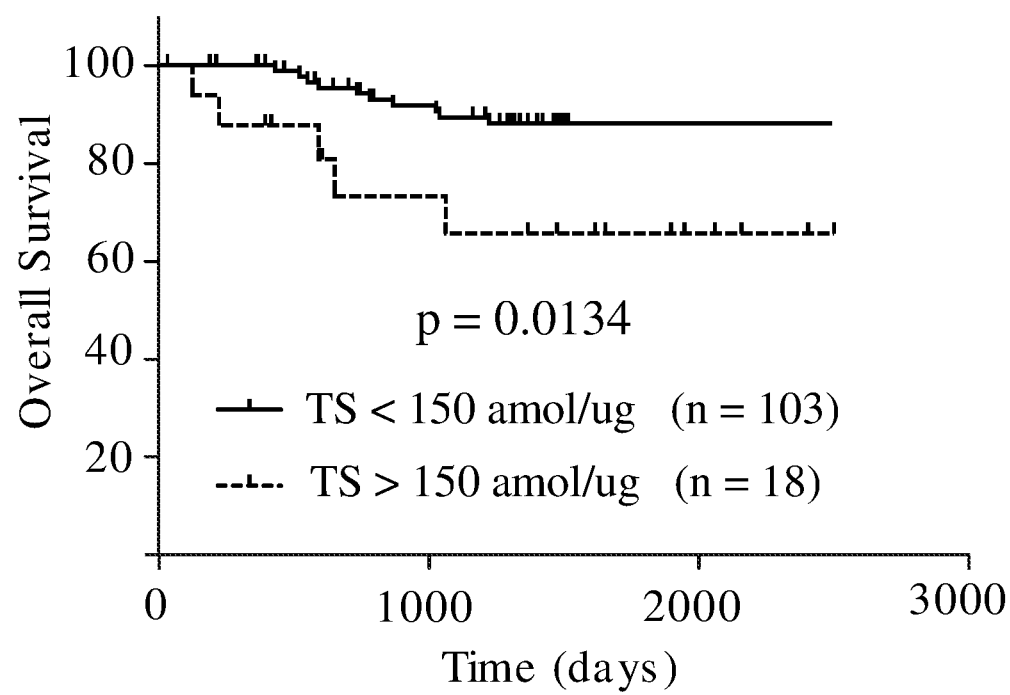
FIG. 2 shows the overall survival curve for NSCLC patients treated with the chemotherapy combination of cisplatin/pemetrexed in relation to TS protein expression levels. Those patients whose tumor cells express detectable levels <150 amol/ug of TS fragment peptide have a more favorable outcome. This overall survival curve shows that those patients whose tumor cells express levels of the TS protein below 150 amol/ug protein analyzed have a much greater possibility of longer overall survival than those patients whose tumor cells express above 150 amol/ug when treated with the combination of cisplatin and pemetrexed. Results are statistically significant with p value=0.0135.
Figure 3:
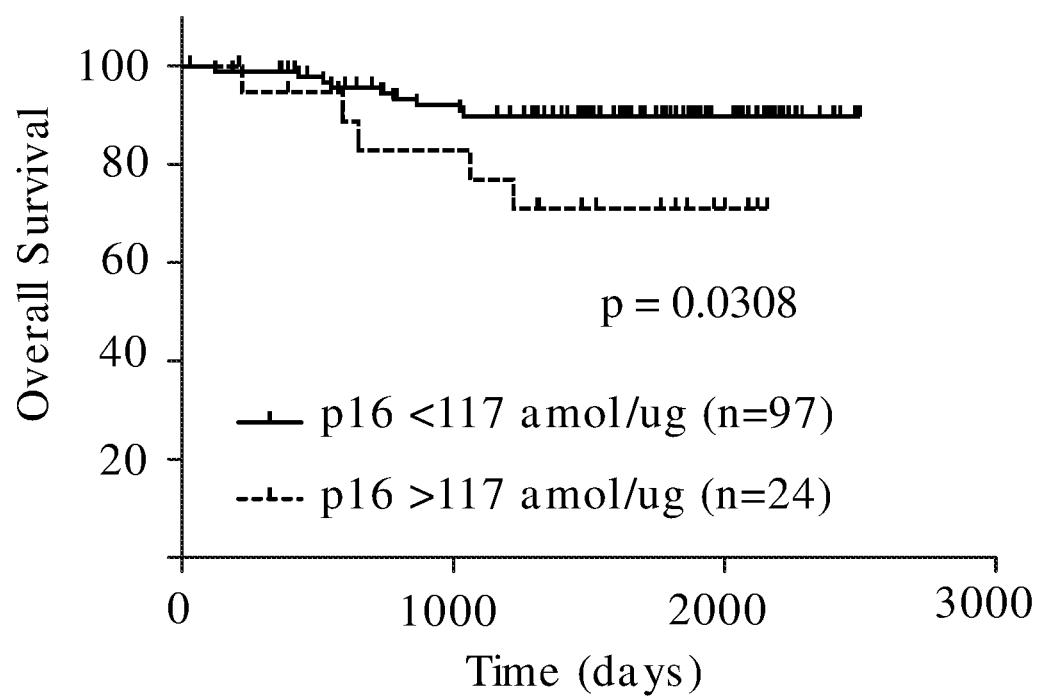
FIG. 3 shows the overall survival curve for NSCLC patients treated with the chemotherapy combination of cisplatin/pemetrexed in relation to p16 protein expression levels. Those patients whose tumor cells express levels <117 amol/ug of the specified p16 fragment peptide have a more favorable outcome. This overall survival curve shows that those patients whose tumor cells express levels of the p16 protein below 117 amol/ug protein analyzed have a much greater possibility of longer overall survival than those patients whose tumor cells express above 117 amol/ug when treated with the combination of cisplatin and pemetrexed. Results are statistically significant with p value=0.0308
Figure 4:
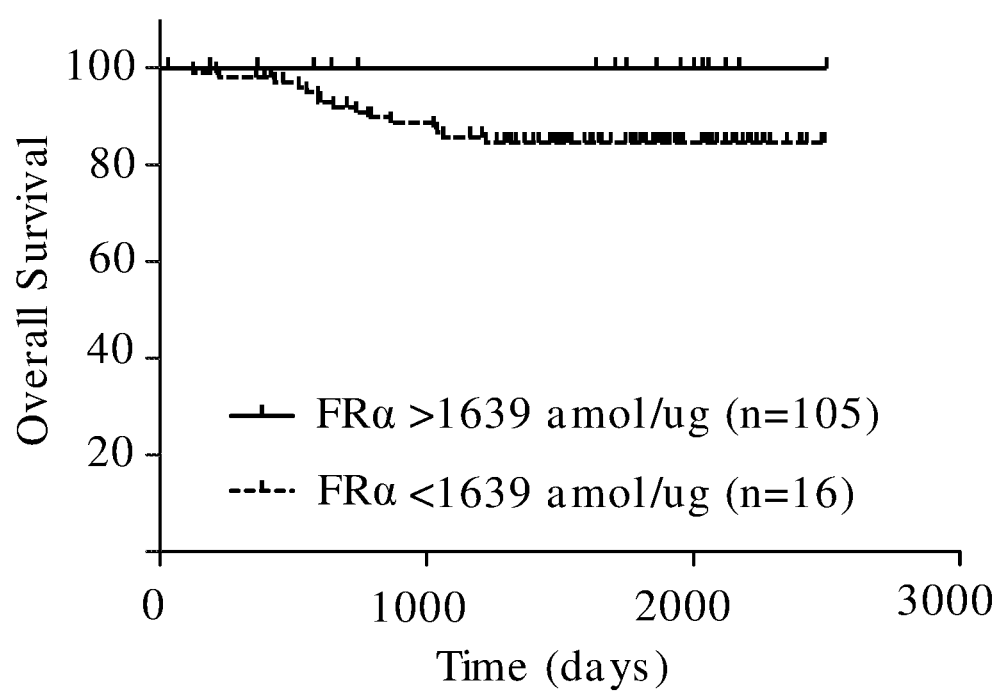
FIG. 4 shows the overall survival curve for NSCLC patients treated with the chemotherapy combination of cisplatin/pemetrexed in relation to FRα protein expression levels. Those patients whose tumor cells express levels >1639 amol/ug of the specified FRα fragment peptide have a more favorable outcome. This overall survival curve shows that those patients whose tumor cells express levels of the FRα protein above 1639 amol/ug protein analyzed have a much greater possibility of longer overall survival than those patients whose tumor cells express below 1639 amol/ug when treated with the combination of cisplatin and pemetrexed.

Improved methods are provided for treating lung cancer patients; more specifically the methods involve determining if a cancer patient, and specifically a NSCLC patient, will clinically respond in a favorable manner to the combination therapy of cisplatin/pemetrexed. Diagnostic methods are provided for measuring the ERCC1, TS, p16, and FRα proteins in a tumor sample or samples from the patient. Advantageously the sample is formalin-fixed tissue. Using an SRM/MRM assay that simultaneously measures specific ERCC1, TS, p16, and FRα peptide fragments, and particular characteristics about the peptides, the amount of the ERCC1, TS, p16, and FRα proteins in cells derived from formalin fixed paraffin embedded (FFPE) tissue is determined. The peptide fragments derive from the full-length ERCC1, TS, p16, and FRα proteins. The peptide sequence for ERCC1 protein is SEQ ID NO:1 EGVPQPSGPPAR, the peptide sequence for TS is SEQ ID NO:2 EEGDLGPVYGFQWR, the peptide sequence for p16 is SEQ ID NO:3 ALLEAGALPNAPNSYGR, and the peptide sequence for FRα is SEQ ID NO:4 DVSYLYR. Surprisingly it has been found that these peptides can be reliably detected and quantitated simultaneously in digests prepared from FFPE samples of tumor tissue. See U.S. patent application Ser. No. 13/993,045, the contents of which are hereby incorporated by reference in their entirety.

More specifically, this SRM/MRM assay can measure these peptides directly in complex protein lysate samples prepared from cells procured from patient tissue samples, such as formalin fixed cancer patient tissue. Methods of preparing protein samples from formalin-fixed tissue are described in U.S. Pat. No. 7,473,532, the contents of which are hereby incorporated by reference in their entirety. The methods described in U.S. Pat. No. 7,473,532 may conveniently be carried out using Liquid Tissue reagents and protocol available from Expression Pathology Inc. (Rockville, Md.).

The most widely and advantageously available form of tissue, and cancer tissue, from cancer patients is formalin fixed, paraffin embedded tissue. Formaldehyde/formalin fixation of surgically removed tissue is by far the most common method of preserving cancer tissue samples worldwide and is the accepted convention in standard pathology practice. Aqueous solutions of formaldehyde are referred to as formalin. "100%" formalin consists of a saturated solution of formaldehyde (this is about 40% by volume or 37% by mass) in water, with a small amount of stabilizer, usually methanol, to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long term storage at room temperature. Thus molecular analytical methods to analyze formalin fixed cancer tissue will be the most accepted and heavily utilized methods for analysis of cancer patient tissue.

Results from the SRM/MRM assay can be used to correlate accurate and precise quantitative levels of the ERCC1, TS, p16, and FRα proteins within the specific cancer of the patient from whom the tissue was collected and preserved, including lung cancer tissue. This not only provides diagnostic/prognostic information about the cancer, but also permits a physician or other medical professional to determine appropriate therapy for the patient. In this case, utilizing these assays can provide information about specific levels of ERCC1, TS, p16, and FRα protein expression simultaneously in cancer tissue and whether or not the patient from whom the cancer tissue was obtained will respond in a favorable way to the combination therapy of cisplatin/pemetrexed.

Treating cancer patients with cisplatin, and most commonly in combination with the drug pemetrexed, is one of the most common and effective strategies for preventing cancer from growing and thus prolonging the lives of cancer patients, especially lung cancer patients. The ERCC1 normally functions to repair damaged DNA and thus helps control how a healthy normal cell grows, divides, and repairs itself. However, in some cancers, including lung cancer, the cancer cells express abnormally high levels of the ERCC1 protein imparting an enhanced ability of the cancer cells to repair and synthesize DNA providing for increased tumor cell growth. It therefore is useful for a clinician to know quantitative levels of the ERCC1 protein in a patient's cancer cells because the chemotherapy agent cisplatin damages the DNA in growing/dividing tumor cells and higher levels of ERCC1 can overcome the effects of cisplatin. Thus abnormally high ERCC1 levels impart resistance to cisplatin therapy.

The TS protein is an enzyme that catalyzes the conversion of deoxyuridine monophosphate (dUMP) to deoxythymidine monophosphate (dTMP). Because thymidine is one of the nucleotides in DNA it is imperative that TS be functional for a cell to synthesize DNA in order to divide. With inhibition of TS, an imbalance of deoxynucleotides and increased levels of dUMP arise causing DNA damage and ultimately cell death. TS-negative NSCLC tumors, prognostically worse without treatment, derive substantial benefit from pemetrexed-based chemotherapy. The mode of action between the p16 protein and the chemotherapy agents cisplatin and pemetrexed is unknown and thus the finding that p16 expression levels below a specified reference level indicates the likelihood of a positive response to the combination of cisplatin/pemetrexed cannot presently be explained. The FRα protein brings folic acid into the cell and thus the folic acid-like chemotherapeutic agent pemetrexed is efficiently transported into the tumor cell via the presence of the FRα protein on the cell surface. Higher expression levels of FRα are indicative of the ability of pemetrexed to enter the tumor cell at a higher rate and capacity which then allows for pemetrexed to inhibit the function of the TS protein.

Presently the most widely-used and applied methodology to determine protein presence in cancer patient tissue, especially FFPE tissue, is immunohistochemistry (IHC). IHC methodology utilizes an antibody to detect the protein of interest. The results of an IHC test are most often interpreted by a pathologist or histotechnologist. This interpretation is subjective and does not provide quantitative data that are predictive of sensitivity to therapeutic agents that target specific oncoprotein targets, such as cisplatin/pemetrexed sensitivity in a ERCC1, TS, p16, and FRα positive tumor cell population.

Research from other IHC assays, such as the Her2 IHC test suggest the results obtained from such tests may be wrong. This is probably because different labs have different rules for classifying positive and negative IHC status. Each pathologist running the tests also may use different criteria to decide whether the results are positive or negative. In most cases, this happens when the test results are borderline, meaning that the results are neither strongly positive nor strongly negative. In other cases, tissue from one area of cancer tissue can test positive while tissue from a different area of the cancer tests negative. Inaccurate IHC test results may mean that patients diagnosed with cancer do not receive the best possible care. If all or part of a cancer is positive for a specific target oncoprotein but test results classify it as negative, physicians are unlikely to recommend the correct therapeutic treatment, even though the patient could potentially benefit from those agents. If a cancer is oncoprotein target negative but test results classify it as positive, physicians may recommend a specific therapeutic treatment, even though the patient is unlikely to get any benefits and is exposed to the agent's secondary risks.

Thus there is great clinical value in the ability to correctly evaluate quantitative levels of the ERCC1, TS, p16, and FRα proteins in tumors, especially lung tumors, so that the patient will have the greatest chance of receiving the most optimal treatment.

Detection of peptides and determining quantitative levels of specified ERCC1, TS, p16, and FRα fragment peptides may be carried out in a mass spectrometer by the SRM/MRM methodology, whereby the SRM/MRM signature chromatographic peak area of each peptide is determined within a complex peptide mixture present in a Liquid Tissue lysate (see U.S. Pat. No. 7,473,532, as described above). Quantitative levels of the ERCC1, TS, p16, and FRα proteins are then measured by the SRM/MRM methodology whereby the SRM/MRM signature chromatographic peak area of an individual specified peptide from each of the ERCC1, TS, p16, and FRα proteins in one biological sample is compared to the SRM/MRM signature chromatographic peak area of a known amount of a "spiked" internal standard for each of the individual specified ERCC1, TS, p16, and FRα fragment peptides. In one embodiment, the internal standard is a synthetic version of the same exact ERCC1, TS, p16, and FRα fragment peptides where the synthetic peptides contain one or more amino acid residues labeled with one or more heavy isotopes. Such isotope labeled internal standards are synthesized so that mass spectrometry analysis generates a predictable and consistent SRM/MRM signature chromatographic peak that is different and distinct from the native ERCC1, TS, p16, and FRα fragment peptide chromatographic signature peaks and which can be used as comparator peaks. Thus when the internal standard is spiked in known amounts into a protein or peptide preparation from a biological sample and analyzed by mass spectrometry, the SRM/MRM signature chromatographic peak area of the native peptide is compared to the SRM/MRM signature chromatographic peak area of the internal standard peptide, and this numerical comparison indicates either the absolute molarity and/or absolute weight of the native peptide present in the original protein preparation from the biological sample. Quantitative data for fragment peptides are displayed according to the amount of protein analyzed per sample.

In order to develop the SRM/MRM assay for the ERCC1, TS, p16, and FRα fragment peptides additional information beyond simply the peptide sequence needs to be utilized by the mass spectrometer. That additional information is important in directing and instructing the mass spectrometer, (e.g., a triple quadrupole mass spectrometer) to perform the correct and focused analysis of the specified ERCC1, TS, p16, and FRα fragment peptides. An important consideration when conducting an SRM/MRM assay is that such an assay may be effectively performed on a triple quadrupole mass spectrometer. That type of a mass spectrometer may be considered to be presently the most suitable instrument for analyzing a single isolated target peptide within a very complex protein lysate that may consist of hundreds of thousands to millions of individual peptides from all the proteins contained within a cell. The additional information provides the triple quadrupole mass spectrometer with the correct directives to allow analysis of a single isolated target peptide within a very complex protein lysate that may consist of hundreds of thousands to millions of individual peptides from all the proteins contained within a cell. Although SRM/MRM assays can be developed and performed on any type of mass spectrometer, including a MALDI, ion trap, ion trap/quadrupole hybrid, or triple quadrupole, presently the most advantageous instrument platform for SRM/MRM assay is often considered to be a triple quadrupole instrument platform. The additional information about target peptides in general, and in particular about the specified ERCC1, TS, p16, and FRα fragment peptides, may include one or more of the mono isotopic mass of each peptide, its precursor charge state, the precursor m/z value, the m/z transition ions, and the ion type of each transition ion. The peptide sequence of the specified ERCC1, TS, p16, and FRα fragment peptides used in the methods described herein is shown in Table 1.

TABLE 1

| SEQ ID NO | Protein | Peptide Sequence |
|---|---|---|
| SEQ ID NO 1 | ERCC1 | EGVPQPSGPPAR |
| SEQ ID NO 2 | TS | EEGDLGPVYGFQWR |
| SEQ ID NO 3 | p16 | ALLEAGALPNAPNSYGR |
| SEQ ID NO 4 | FRα | DVSYLYR |

To determine an appropriate reference level for ERCC1, TS, p16, and FRα quantitation, tumor samples are obtained from a cohort of patients suffering from cancer, in this case lung cancer. The lung tumor samples are formalin-fixed using standard methods and the level of ERCC1, TS, p16, and FRα in the samples is measured using the methods as described above. The tissue samples may also be examined using IHC and FISH using methods that are well known in the art. The patients in the cohort are treated with the combination of cisplatin and pemetrexed therapeutic agents and the response of the patients is measured using methods that are well known in the art, for example by recording the overall survival of the patients at time intervals after treatment. A suitable reference level can be determined using statistical methods that are well known in the art, for example by determining the lowest p value of a log rank test. Once a reference level has been determined it can be used to identify those patients whose ERCC1, TS, p16, and FRα expression levels indicate that they may likely benefit from the combination of the combination cisplatin/pemetrexed therapeutic regimen. The skilled artisan will recognize that cisplatin/pemetrexed is the most common treatment regimen for NSCLC patients. Levels of ERCC1, TS, p16, and FRα proteins in patient tumor samples are typically expressed in amol/µg, although other units can be used. The skilled artisan will recognize that a reference level can be expressed as a range around a central value, for example, +/−250, 150, 100, 50 or 25 amol/µg.

For those patients where protein expression as measured using the methods described herein indicates that treatment with cisplatin plus pemetrexed is unlikely to be effective, an alternative therapeutic regimen may be used. Other therapeutics regimens include surgery (including wedge resection, segmental resection, lobectomy and pneumonectomy), radiation therapy, and targeted drug therapy (such as treatment with Afatinib (Gilotrif), Bevacizumab (Avastin), Ceritinib (Zykadia), Crizotinib (Xalkori), Erlotinib (Tarceva), Nivolumab (Opdivo) and Ramucirumab (Cyramza)).

Because both nucleic acids and protein can be analyzed from the same Liquid Tissue biomolecular preparation it is possible to generate additional information about disease diagnosis and drug treatment decisions from the nucleic acids in same sample upon which proteins were analyzed. For example, if the ERCC1, TS, p16, and FRα proteins are expressed by certain cells at increased levels, when assayed by SRM the data can provide information about the state of the cells and their potential for uncontrolled growth, choice of optimal therapy, and potential drug resistance. At the same time, information about the status of genes and/or the nucleic acids and proteins they encode (e.g., mRNA molecules and their expression levels or splice variations) can be obtained from nucleic acids present in the same Liquid Tissue™ biomolecular preparation. Nucleic acids can be assessed simultaneously to the SRM analysis of proteins, including the ERCC1, TS, p16, and FRα proteins. In one embodiment, information about the ERCC1, TS, p16, and FRα proteins and/or one, two, three, four or more additional proteins may be assessed by examining the nucleic acids encoding those proteins. Those nucleic acids can be examined, for example, by one or more, two or more, or three or more of: sequencing methods, polymerase chain reaction methods, restriction fragment polymorphism analysis, identification of deletions, insertions, and/or determinations of the presence of mutations, including but not limited to, single base pair polymorphisms, transitions, transversions, or combinations thereof.

The invention claimed is:

1. A method of treating a patient suffering from lung cancer comprising:
    (a) quantifying a level of at least one of a group of peptides selected from the group consisting of: an ERCC1 fragment peptide having an amino acid sequence as set forth in SEQ ID NO:1, a TS fragment peptide having an amino acid sequence as set forth in SEQ ID NO:2, a p16 fragment peptide having an amino acid sequence as set forth in SEQ ID NO:3, and a FRα fragment peptide having an amino acid sequence as set forth in SEQ ID NO:4,
    in a protein digest prepared from a formalin fixed tumor sample obtained from the patient and calculating the level of said ERCC1, TS, p16, and/or FRα fragment peptides in said formalin fixed tumor sample by selected reaction monitoring using mass spectrometry;
    (b) comparing the level of said ERCC1, TS, p16, and/or FRα fragment peptides to a reference level, and
    (c) treating the patient with a therapeutic regimen comprising an effective amount of a combination of cisplatin and pemetrexed therapeutic agents when the level of the ERCC1 fragment peptide is below said reference level, wherein said reference level of the ERCC1 fragment peptide is 36±25 amol/ug protein analyzed, or
    (d) treating the patient with a therapeutic regimen comprising an effective amount of a combination of cisplatin and pemetrexed therapeutic agents when the level of the TS fragment peptide is below said reference level, wherein said reference level of the TS fragment peptide is 150±50 or 150±25 amol/ug protein analyzed, or
    (e) treating the patient with a therapeutic regimen comprising an effective amount of a combination of cisplatin and pemetrexed therapeutic agents when the level of the p16 fragment peptide is below said reference level, wherein said reference level of the p16 fragment peptide is 117±50 or 117±25 amol/ug protein analyzed, or
    (f) treating the patient with a therapeutic regimen comprising an effective amount of a combination of cisplatin and pemetrexed therapeutic agents when the level of the FRα fragment peptide is above said reference level, wherein the reference level of the FRα fragment peptide is 1639±250, 1639±150, 1639±100, 1639±50 or 1639±25 amol/ug protein analyzed; or
    (g) treating the patient with an alternative therapeutic regimen selected from the group consisting of surgery, radiation therapy, and targeted drug therapy when the level of the ERCC1 fragment peptide is at or above 36±25 amol/ug protein analyzed; or when the level of the TS fragment peptide is at or above 150±50 or 150±25 amol/ug protein analyzed; or when the p16 fragment peptide is at or above 117±50 or 117±25 amol/ug protein analyzed; or when the FRα fragment peptide is at or below 1639±250, 1639±150, 1639±100, 1639±50 or 1639±25 amol/ug protein analyzed.

2. The method according to claim 1, wherein at least two of said fragment peptides are quantified.

3. The method of claim 1, wherein said protein digest comprises a protease digest.

4. The method of claim 1, wherein the mode of mass spectrometry used is Selected Reaction Monitoring (SRM), Multiple Reaction Monitoring (MRM), Parallel Reaction Monitoring (PRM), intelligent Selected Reaction Monitoring (iSRM), and/or multiple Selected Reaction Monitoring (mSRM).

5. The method of claim 1, wherein the tissue is paraffin embedded tissue.

6. The method of claim 1, wherein quantifying the ERCC1 fragment peptide comprises determining an amount of the ERCC1 fragment peptide in said sample by comparing to a spiked internal standard peptide of known amount, wherein both the native peptide in the sample and the internal standard peptide corresponds to the same amino acid sequence of the ERCC1 fragment peptide as shown in SEQ ID NO:1.

7. The method of claim 1, wherein quantifying the TS fragment peptide comprises determining an amount of the TS peptide in said sample by comparing to a spiked internal standard peptide of known amount, wherein both the native peptide in the sample and the internal standard peptide corresponds to the same amino acid sequence of the TS fragment peptide as shown in SEQ ID NO:2.

8. The method of claim 1, wherein quantifying the p16 fragment peptide comprises determining an amount of the p16 peptide in said sample by comparing to a spiked internal standard peptide of known amount, wherein both the native peptide in the sample and the internal standard peptide corresponds to the same amino acid sequence of the p16 fragment peptide as shown in SEQ ID NO:3.

9. The method of claim 1, wherein quantifying the FRα fragment peptide comprises determining an amount of the FRα peptide in said sample by comparing to a spiked internal standard peptide of known amount, wherein both the native peptide in the sample and the internal standard peptide corresponds to the same amino acid sequence of the FRα fragment peptide as shown in SEQ ID NO:4.

10. The method of claim 1, wherein quantifying the fragment peptide comprises determining an amount of said peptide in said sample by comparing to a spiked internal standard peptide of known amount, wherein both the native peptide in the sample and the internal standard peptide corresponds to the same amino acid sequence and wherein the internal standard peptide is an isotopically labeled peptide, wherein the isotopically labeled internal standard peptide comprises one or more heavy stable isotopes selected from the group consisting of $^{18}O$, $^{17}O$, $^{15}N$, $^{13}C$, $^{2}H$ and a combination thereof.

* * * * *